(12) United States Patent
Cohen

(10) Patent No.: US 8,506,545 B2
(45) Date of Patent: Aug. 13, 2013

(54) ABSORBENT PAD

(75) Inventor: Richmond R. Cohen, Williamsport, PA (US)

(73) Assignee: First Quality Products, Inc., Great Neck, NY (US)

( * ) Notice: Subject to any disclaimer, the term of this patent is extended or adjusted under 35 U.S.C. 154(b) by 629 days.

(21) Appl. No.: 12/343,890

(22) Filed: Dec. 24, 2008

(65) Prior Publication Data

US 2010/0160885 A1    Jun. 24, 2010

(51) Int. Cl.
*A61F 13/15* (2006.01)
*A61F 13/20* (2006.01)

(52) U.S. Cl.
USPC ...................................... 604/385.27; 604/378

(58) Field of Classification Search
USPC ............................ 604/385.24–385.29, 385.22
See application file for complete search history.

(56) References Cited

U.S. PATENT DOCUMENTS

| | | | |
|---|---|---|---|
| 4,589,876 A | 5/1986 | Van Tilburg | |
| 5,558,663 A | 9/1996 | Weinberger et al. | |
| 5,713,886 A | 2/1998 | Sturino | |
| 6,462,251 B1 | 10/2002 | Cimini et al. | |
| 7,172,584 B2 | 2/2007 | Karami | |
| 2003/0028167 A1* | 2/2003 | Kashiwagi et al. | 604/385.04 |
| 2003/0139724 A1* | 7/2003 | Ragnarson et al. | 604/385.08 |

FOREIGN PATENT DOCUMENTS

| WO | WO9312747 A1 | 7/1993 |
|---|---|---|
| WO | WO9513035 A1 | 5/1995 |

OTHER PUBLICATIONS

International Search Report of PCT/US2009/069430 dated Mar. 1, 2010.
Written Opinion of the International Searching Authority dated Mar. 1, 2010.
Supplementary European Search Report dated May 8, 2013.

\* cited by examiner

*Primary Examiner* — Melanie Hand
(74) *Attorney, Agent, or Firm* — Amster, Rothstein & Ebenstein LLP

(57) ABSTRACT

An absorbent pad including a chassis having a first side edge and a second side edge. The chassis includes a liquid pervious topsheet and a liquid impervious backsheet. An absorbent system is disposed between the topsheet and the backsheet. An elastic element is disposed along each of the first and second side edges of the chassis and attached to at least one of the topsheet and the backsheet, the elastic elements generating a cupping action so that the absorbent pad is biased towards a cup-like shape. A first side adhesive element is attached to the chassis inwardly from the first side edge of the chassis. A second side adhesive element is attached to the chassis inwardly from the second side edge of the chassis. A central adhesive element is attached to the chassis between the first and second side adhesive elements. The absorbent pad has a first configuration in which the central adhesive element is releasably attached to an inner surface of an undergarment so that the absorbent pad retains its cup-like shape and a second configuration in which the first and second side adhesive elements are releasably attached to an outer surface of the undergarment to overcome the cupping action of the elastic elements.

14 Claims, 3 Drawing Sheets

ABSORBENT PAD

FIELD OF THE INVENTION

The present invention relates to disposable absorbent pads having absorbent inserts, and more specifically to disposable absorbent pads having mechanisms for attachment to the user's undergarment.

BACKGROUND OF THE INVENTION

For convenience, discreetness and protection, women who are menstruating or who have very light incontinence issues may wear disposable absorbent articles such as pantiliners and sanitary napkins. When these women are ambulatory and/or wear the articles for long periods of time, the pads may shift from their original position and buckle, fold, or crumple. Further, the products may be distorted or twisted significantly and may even be dislodged completely. Such displacement, if it occurs prior to an episode of incontinence, may hinder the pad's ability to accept the bodily fluid from the user, which may result in leakage and wetness.

Conventional feminine pads, pantiliners and sanitary napkins are equipped with a backing strip of adhesive. The adhesive strip is pressed against the inside of the user's undergarment to hold the product in place during use. Although the adhesive provides considerable containment of the pad's position, it is not completely effective. The efficacy of the adhesive is compromised by the user's movement, particularly when the adhesive is exposed to wetness.

To provide improved stability, many feminine hygiene articles include wings to keep the articles in place. The wings are typically lateral extensions of the topsheet and backsheet materials extending from the crotch portion of the article. After the user attaches the backing strip to the undergarment, the wings may be folded back underneath the undergarment. The wings may overlap one another, and there is at least one attachment means associated with at least one of the wings to secure the wings to one another or to the underside of the undergarment. The attachment of the wings to the underside of the undergarment provides additional fastening to maintain the article in position during use.

Wings may be used in both feminine hygiene articles and bladder control pads. However, there are some risks associated with using such pads with wings for trapping and retaining urine, particularly during heavy periods of incontinence. In particular, because such pads with wings have lateral extensions of material beyond the crotch width of the pad, the wings preclude the use of any elastic means along the lateral crotch portions of the pads. Such elastic means assist in cupping and shaping the pads during use and are crucial in preventing leaks. Thus, since these bladder control pads with wings do not have elastic means, they are not particularly effective at retaining urine. Further, when the wings are deployed, the side edges of the pad are drawn away from the perineal area of the user, potentially encouraging more runoff after an episode of incontinence while wearing the pad.

SUMMARY OF THE INVENTION

An absorbent pad according to an exemplary embodiment of the present invention comprises a chassis having a first side edge and a second side edge, the chassis comprising a liquid pervious topsheet and a liquid impervious backsheet. The absorbent pad further comprises: an absorbent system disposed between the topsheet and the backsheet; an elastic element disposed along each of the first and second side edges of the chassis and attached to at least one of the topsheet and the backsheet, the elastic elements generating a cupping action so that the absorbent pad is biased towards a cup-like shape; a first side adhesive element attached to the chassis inwardly from the first side edge of the chassis; a second side adhesive element attached to the chassis inwardly from the second side edge of the chassis; and a central adhesive element attached to the chassis between the first and second side adhesive elements, the absorbent pad having a first configuration in which the central adhesive element is releasably attached to an inner surface of an undergarment so that the absorbent pad retains its cup-like shape and a second configuration in which the first and second side adhesive elements are releasably attached to an outer surface of the undergarment to overcome the cupping action of the elastic elements.

In at least one embodiment, the absorbent pad further comprises a first side peel strip that covers the first side adhesive element; a second side peel strip that covers the second side adhesive element; and a central peel strip that covers the central adhesive element.

In at least one embodiment, the absorbent system comprises an absorbent core.

In at least one embodiment, the absorbent system comprises an acquisition/distribution layer disposed over the absorbent core.

In at least one embodiment, the absorbent core comprises at least one of cellulosic fibers and superabsorbent material.

In at least one embodiment, the backsheet comprises at least one of a polymeric film layer and a nonwoven material layer.

In at least one embodiment, the topsheet comprises a nonwoven material.

A method of forming an absorbent pad according to an exemplary embodiment of the present invention comprises the steps of: forming a liquid pervious topsheet from a topsheet material web; forming a liquid impervious backsheet from a backsheet material web; forming a layered structure comprising an absorbent system disposed between the backsheet and the topsheet, the layered structure having a first side edge and a second side edge; attaching an elastic element to at least one of the topsheet and the backsheet along each of the first and second side edges of the layered structure, the elastic elements generating a cupping action so that the absorbent pad is biased towards a cup-like shape; attaching a first side adhesive element to the layered structure inwardly from the first side edge of the layered structure; attaching a second side adhesive element to the layered structure inwardly from the second side edge of the layered structure; and attaching a central adhesive element to the layered structure between the first and second side adhesive elements, the absorbent pad having a first configuration in which the central adhesive element is releasably attached to an inner surface of an undergarment so that the absorbent pad retains its cup-like shape and a second configuration in which the first and second side adhesive elements are releasably attached to an outer surface of the undergarment to overcome the cupping action of the elastic elements.

In at least one embodiment, the method further comprises the steps of: covering the first side adhesive element with a first side peel strip; covering the second side adhesive element with a second side peel strip; and covering the central adhesive element with a central peel strip.

In at least one embodiment, the step of forming the layered structure comprises laminating the topsheet, backsheet and absorbent system together to form a unitary structure.

In at least one embodiment, the absorbent system comprises an absorbent core.

In at least one embodiment, the absorbent system comprises an acquisition/distribution layer disposed over the absorbent core.

In at least one embodiment, the topsheet material comprises a nonwoven material layer.

In at least one embodiment, the backsheet material comprises at least one of a nonwoven material layer and a polymeric film layer.

BRIEF DESCRIPTION OF THE DRAWINGS

The above and related objects, features and advantages of the present invention will be more fully understood by reference to the following detailed description of the presently preferred, albeit illustrative, embodiments of the present invention when taken in conjunction with the accompanying drawings wherein.

DETAILED DESCRIPTION OF PREFERRED EMBODIMENTS

The present invention is directed to an absorbent pad that can be used in at least two different configurations depending on the needs of the user. In particular, according to various exemplary embodiments of the present invention, an absorbent pad is provided that is biased towards a cup-like configuration and which can also be altered to take on a flatter configuration in which lateral sides of the absorbent pad are adhered to the outer surface of the user's undergarment. The cup-like configuration of the inventive absorbent pad may be useful during the night when there may be larger or multiple voids, and the flatter configuration may be useful during the day when there may be lighter volumes and a more secure attachment is desired.

Figure 1:
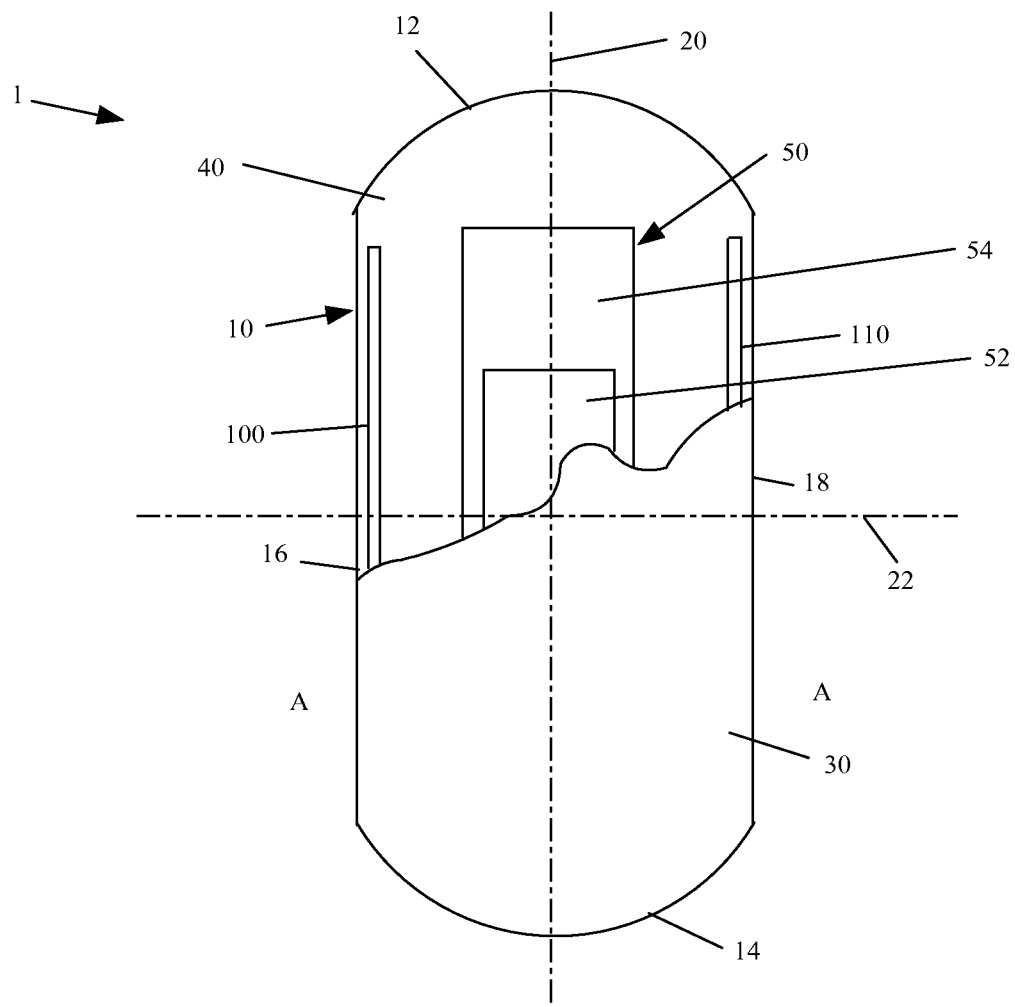
FIG. 1 is a top elevational view of an absorbent pad according to an exemplary embodiment of the present invention with the topsheet partially removed.
Figure 2:
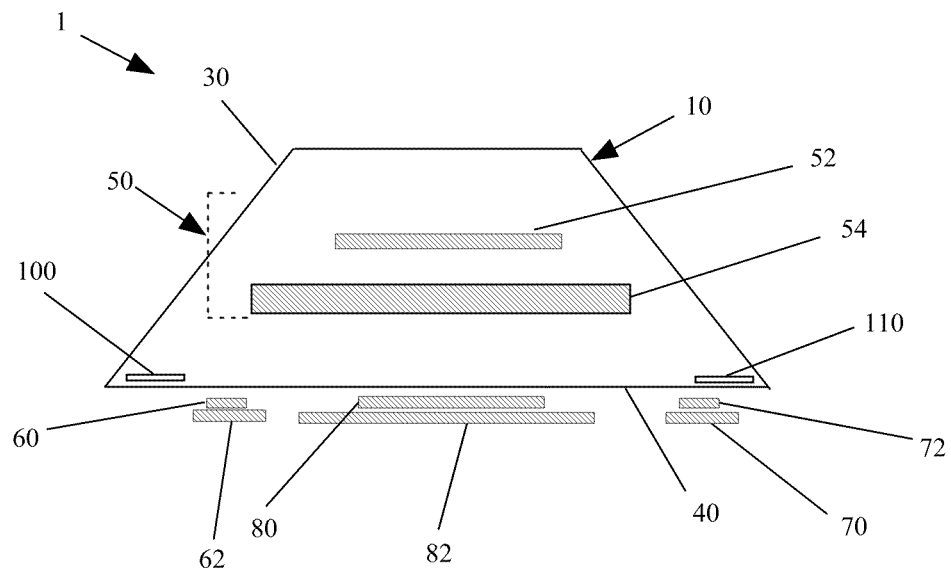
FIG. 2 is a cross-sectional view of an absorbent pad according to an exemplary embodiment of the present invention taken along the transverse centerline 22 in FIG. 1.
Figure 3:
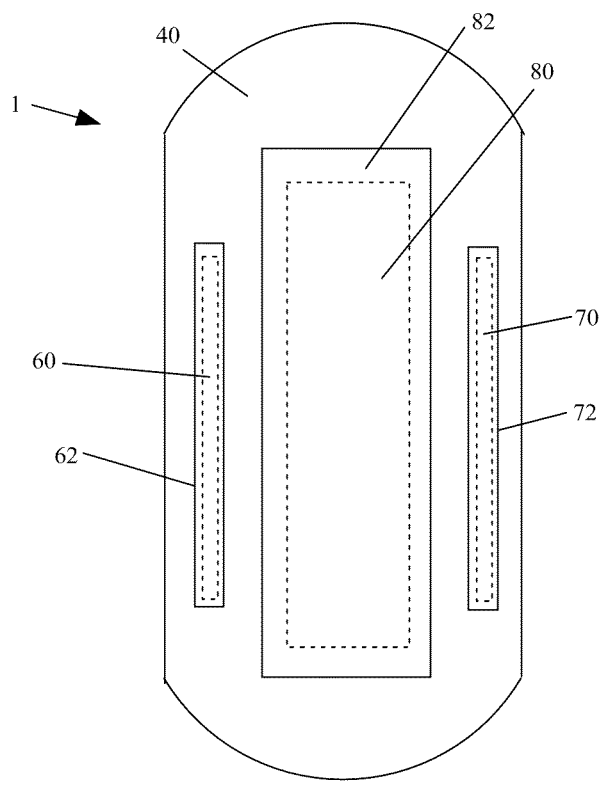
FIG. 3 is a bottom plan view of an absorbent pad according to an exemplary embodiment of the present invention.
Figure 4:
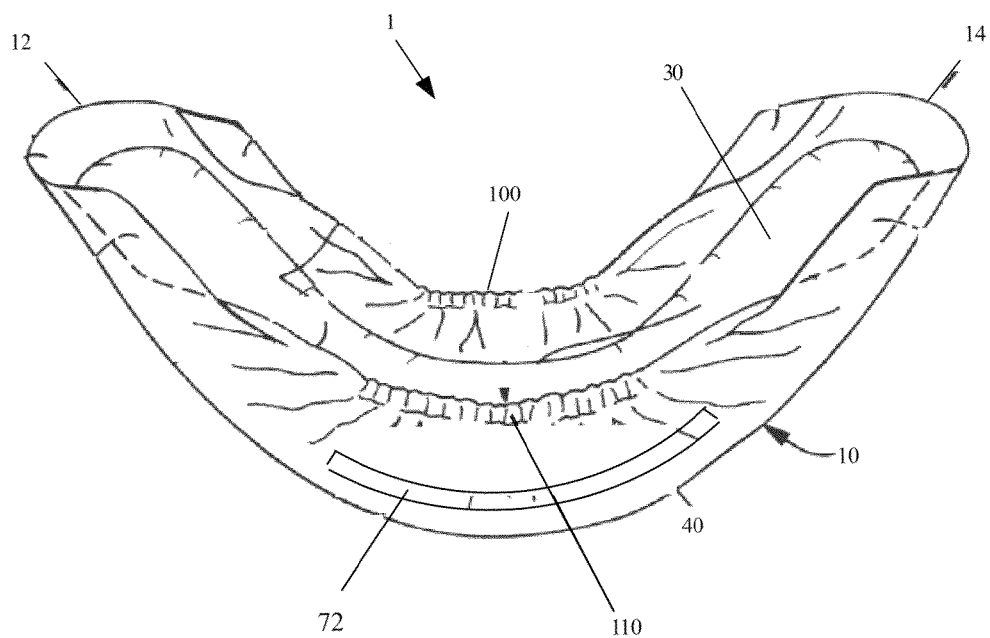
FIG. 4 is a perspective view showing an absorbent pad according to an exemplary embodiment of the present invention having a cup-like configuration.
Figure 5:
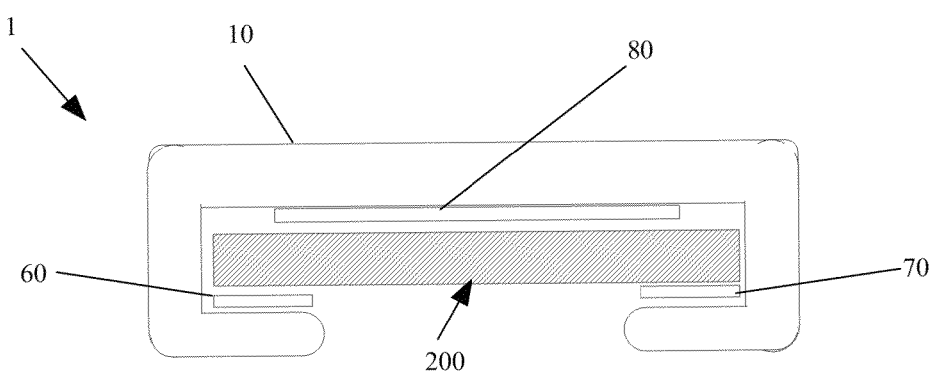
FIG. 5 is a cross-sectional view showing an absorbent pad according to an exemplary embodiment of the present invention having a flattened configuration after being attached to an undergarment.

FIGS. 1-5 show the absorbent pad, generally designated by reference number 1, according to an exemplary embodiment of the present invention. FIG. 1 is a top elevational view of the absorbent pad 1 with the topsheet partially removed; FIG. 2 is a cross-sectional view of the absorbent pad 1 taken along the transverse centerline 22 in FIG. 1; FIG. 3 is a bottom plan view of the absorbent pad 1; FIG. 4 is a perspective view of the absorbent pad 1 in a cup-like configuration; and FIG. 5 is a cross-sectional view of the absorbent pad 1 attached to an undergarment 200 so as to overcome the cupping action of the absorbent pad 1.

The absorbent pad 1 includes a main body 10 having a front edge 12 defining a front portion of the absorbent pad 1 and a back edge 14 defining a rear portion of the absorbent pad 1. Each of the front and back edges 12, 14 are arcuate in shape. The main body 10 also has a first side edge 16 and a second side edge 18.

The absorbent pad 1 has an imaginary longitudinal centerline 20 bisecting the absorbent pad 1 in two identical halves and an imaginary transverse centerline 22 perpendicular to the longitudinal centerline 20.

As shown in FIGS. 1-5, the main body 10 is of a laminate construction and preferably includes a fluid-permeable topsheet 30, a fluid-impervious backsheet 40 and an absorbent system 50 disposed between the topsheet 30 and the backsheet 40. The topsheet 30 and backsheet 40 form a chassis. As explained in further detail below, each of these components may be made up of one or more layers.

As shown in FIG. 3, the bottom surface of the main body 10 includes a first side adhesive element 60 disposed slightly inwards from the first side edge 16 and a second side adhesive element 70 disposed slightly inwards from the second side edge 18 of the main body 10. The main body 10 also includes a central adhesive element 80 disposed between the first and second side adhesive elements 60, 70 and extending substantially along the longitudinal centerline 20 of the main body 10. In the exemplary embodiment shown in FIG. 3, the transverse centerline 22 of the main body 10 bisects the first and second side adhesive elements 60, 70 and central adhesive element 80 into two halves having equal lengths. Preferably, the central adhesive element 80 extends along substantially the entire longitudinal length of the main body 10 and the first and second side adhesive elements 60, 70 extend along a portion of the first and second side edges 16, 18 of the main body 10. A first side peel strip 62, a second side peel strip 72 and a central peel strip 82 may be applied to the first side adhesive element 60, the second side adhesive element 70 and the central adhesive element 80, respectively, to protect the adhesive elements prior to use. The first side, second side and central peel strips 62, 72, 82 may be made of, for example, siliconized paper.

The main body 10 further includes a first elastic element 100 extending parallel to and between the first side adhesive element 60 and the first side edge 16, and a second elastic element 110 extending parallel to and between the second side edge 18 and second side adhesive element 70. As shown in FIG. 4, when in their naturally contracted state, the first and second elastic elements 100, 110 cause a "cupping action", in that the absorbent pad 10 is pulled into a cup-like shape by the first and second elastic elements 100, 110. The first and second elastic elements 100, 110 may be composed of multiple elastic strands made of any suitable elastic material, such as, for example, synthetic rubber materials, elastic foams, elastic films, elastic nonwovens or other materials known in the art. Preferably, the first and second elastic elements 100, 110 are laminated between the topsheet 30 and the backsheet 40.

The functionality of the absorbent pad 1 will now be described. When a user expects heavier voids and/or the user does not expect to be moving around, for example during the night time, only the central peel strip 82 may be removed to expose the central adhesive element 80 and the absorbent pad 1 may then be pressed down onto the inner surface of the user's undergarment so that the absorbent pad 1 is held in place by the action of the central adhesive element 80. In this configuration, the side peel strips 62, 72 are not removed, and the absorbent pad 1 retains its cup-like shape due to the cupping action of the first and second elastic elements 100, 110. During the day, or when lighter voids are expected, the first and second side peel strips 62, 72 may be removed to expose the first and second side adhesive elements 60, 70. As shown in FIG. 5, the first and second side adhesive elements 60, 70 may then be folded downwards and adhered to the outer surface of the user's undergarment 200. In this configuration, the adherence of the first and second side adhesive elements 60, 70 to the undergarment outer surface overcome the cupping action of the first and second elastic elements 100, 110. Although the absorbent pad 1 does not retain its cup-like shape in this configuration and thus does not provide as much protection, the action of the first and second adhesive elements 60, 70 provide a more secure attachment to the undergarment 200 so that the user feels more secure when moving around.

The topsheet 30 may be a relatively low density, bulky, high-loft non-woven web material. The nonwoven may be spunbond, meltblown, spunbond/meltblown/spunbond, carded and thermobonded or bonded by some other means known in the art. The topsheet 30 may be composed of only one type of fiber, such as polyester or polypropylene or it may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof.

Bi-component fibers may be made up of a polyester layer and a polyethylene sheath. The use of appropriate bi-component materials results in a fusible non-woven fabric. Using a fusible fabric increases the ease with which the topsheet 30 may be mounted to the adjacent absorbent system 50 and/or to the backsheet 40.

The topsheet 30 preferably has a relatively high degree of wettability, although the individual fibers comprising the cover may not be particularly hydrophilic. The topsheet material may also contain a great number of relatively large pores. This is because the topsheet 30 is intended to take-up body fluid rapidly and transport it away from the body and the point of deposition. Therefore, the topsheet 30 contributes little to the time taken for the napkin to absorb a given quantity of liquid (penetration time). Advantageously, the fibers which make up the topsheet 30 should not lose their physical properties when they are wetted, in other words they should not collapse or lose their resiliency when subjected to water or body fluid. The topsheet 30 may be treated to allow fluid to pass through it readily. The topsheet 30 also functions to transfer the fluid quickly to the other layers of the absorbent pad 1. Thus, the topsheet 30 is advantageously wettable, hydrophilic and porous. When composed of synthetic hydrophobic fibers such as polypropylene, polyethylene or bi-component fibers, the topsheet 30 may be treated with a surfactant to impart the desired degree of wettability.

Alternatively, the topsheet 30 can also be made of polymer film having large pores. Because of such high porosity, the film accomplishes the function of quickly transferring body fluid to the inner layers of the absorbent pad 1.

The topsheet 30 may be embossed to the layers of the absorbent system 50 in order to aid in promoting hydrophilicity by fusing the topsheet 30 to the immediately adjacent layer of the absorbent system 50. Such fusion may be effected locally, at a plurality of sites or over the entire contact surface of the topsheet 30. Alternatively, the topsheet 30 may be attached to the absorbent system 50 by other means such as by adhesion.

The absorbent system 50 may be made up of an acquisition/distribution layer (ADL) 52 and an absorbent core 54 disposed below the ADL 52. The ADL 52 receives body fluid from the topsheet 30 and holds it until the underlying absorbent core 54 has an opportunity to absorb the fluid.

The ADL 52 may be more dense and have a larger proportion of smaller pores than the topsheet 30. These attributes allow the ADL 52 to contain body fluid and hold it away from the outer side of the topsheet 30, thereby preventing the fluid from re-wetting the topsheet 30 and its surface. However, the ADL 52 is not so dense as to prevent the passage of the fluid through the ADL 52 into the underlying absorbent core 54.

The ADL 52 may be composed of fibrous materials, such as wood pulp, polyester, rayon, flexible foam, or the like, or combinations thereof. The ADL 52 may also comprise thermoplastic fibers for the purpose of stabilizing the layer and maintaining its structural integrity. The ADL 52 may be treated with surfactant on one or both sides in order to increase its wettability, although generally the ADL 52 is relatively hydrophilic and may not require treatment. In an exemplary embodiment, the ADL 52 is an apertured film including a polyolefin that is rendered wettable by the use of a hydrophilic additive. The ADL 52 is preferably bonded on both sides to the adjacent layers, i.e. the topsheet 30 and the underlying absorbent core 54.

The absorbent core 54 may be composed of a blend or mixture of cellulosic fibers and superabsorbent disposed in and amongst the fibers. Cellulosic fibers that may be used in the absorbent core 54 are well known in the art and include wood pulp, cotton, flax and peat moss. The absorbent core 54 may contain any superabsorbent polymer (SAP), which SAPs are well known in the art. The superabsorbent polymer particles may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. The absorbent core 54 may be made up of multiple layers of absorbent material, and may further include one or more layers of tissue. In an exemplary embodiment, the absorbent core 54 is made up of two layers, including a rectangular first core and a contoured second core.

In a specific example, the absorbent core 54 is a material containing from about 50 to about 90 weight percent cellulosic fibers and, more specifically from about 60 to about 80 weight percent cellulosic fibers. Such a material may contain from about 5 to about 60 weight percent SAP, preferably from about 20 to about 55 weight percent SAP, even more preferably from about 30 to about 45 weight percent SAP, and most preferably about 40 weight percent SAP. The absorbent core 54 can be manufactured by using air-laying means well known in the art.

The backsheet 40 may be composed of a liquid-impervious film material so as to prevent liquid that is entrapped in the absorbent system 50 from egressing the absorbent pad 1 and staining the wearer's undergarment. The backsheet 40 is preferably made of polymeric film, although it may be made of liquid impervious, air-permeable material such as repellent-treated non-woven or microporous films or foams. Alternatively, the backsheet 40 may be made up of a nonwoven material laminated to a thin film material.

In an exemplary embodiment of the present invention, the peel strength from the central adhesive element is about 60 g/in. to 260 g/in. Preferably, the peel strength from the central adhesive element ranges from about 60 g/in. to about 160 g/in., and more preferably, the peel strength ranges from about 90 g/in. to 140 g/in. The peel strength is measured according to the test method described below.

Peel-Test Measurement

The 90°-peel test measurement is executed on an INSTRON model 4443 or equivalent, equipped with a 90°-peel test fixture attached at the machine base instead of the lower grip. The support bar for the 90° pulley mounts to the top of the machine crosshead. In the test, the jaw is separated from the fixture at a constant rate of extension of 12"/min. from an initial separation distance of 1". The full-scale load is 5 N. A test sample is prepared by first taking a bladder control pad and removing the absorbent core from the backsheet, while keeping the end-seal area attached. After scraping off the excess fluff, the test samples are cut into 5.5" long by 1" wide strips, centered along the positioning adhesive. A length of 1.5" is marked from the leading end of the product, and then a 4" mark is made beyond the length of the initial mark. The first 1.5" is the portion of the sample inserted into the upper roller grip, while the 4" long section represents the test area. Then, 4" lengths of the samples are marked to designate the areas to be tested. Next, 6" long by 1.5" wide strips of cotton pants are cut. The cotton strips are next attached to the 90° test fixture plate using double-sided tape. After removing the peel strip, the sample is attached to the cotton pant strip with no applied pressure. After attachment, the sample is subjected to 3 rolls from a 4.5 pound rubber-coated, hand-operated roller. After inserting the 1.5" end of the sample into the upper grip, the peel commences and finishes when the full 4" length is peeled. The average load is recorded as the peel strength.

In an exemplary embodiment of the invention, the elastic elements extend beyond the longitudinal position of the backing adhesive on at least one end of the pad. Such a configuration enables superior cupping of the pad, preventing the occurrence of leakage, and provides more robust edge elements for the pad to prevent leaks in case the user positions the pad in the undergarment at a location that is not centered longitudinally. Also, at least one supplementary elastic element on each side of the pad may extend at least partially along its length underneath a portion of the absorbent core. Placement of these additional elements of elastic underneath a portion of the core further enhances the cupping action on the pad.

Now that the preferred embodiments of the present invention have been shown and described in detail, various modifications and improvement thereon will become readily apparent to those skilled in the art. Accordingly, the spirit and scope of the present invention is to be construed broadly and limited only by the appended claims, and not by the foregoing specification.

What is claimed is:

1. An absorbent pad, comprising: a chassis having a front edge, a back edge, a first side edge extending in a straight line from the front edge to the back edge and a second side edge extending in a straight line from the front edge to the back edge, the chassis comprising: a liquid pervious topsheet; and a liquid impervious backsheet; an absorbent system disposed between the topsheet and the backsheet; an elastic element disposed along each of the first and second side edges of the chassis and attached to at least one of the topsheet and the backsheet and disposed between the topsheet and the backsheet, the elastic elements generating a cupping action so that the absorbent pad is biased towards a cup-like shape; a first side adhesive element attached to the chassis inwardly from the first side edge of the chassis and extending along substantially the entire length of the first side edge; a second side adhesive element attached to the chassis inwardly from the second side edge of the chassis and extending along substantially the entire length of the second side edge; and a central adhesive element attached to the chassis between the first and second side adhesive elements, the absorbent pad having a first configuration in which the central adhesive element is releasably attached to an inner surface of an undergarment so that the absorbent pad retains its cup-like shape and a second configuration in which the first and second side adhesive elements are releasably attached to an outer surface of the undergarment to overcome the cupping action of the elastic elements; wherein the first and second side edges extend in said straight lines when the cupping action is overcome or when the pad is in a flat configuration.

2. The absorbent pad of claim 1, further comprising:
a first side peel strip that covers the first side adhesive element;
a second side peel strip that covers the second side adhesive element; and
a central peel strip that covers the central adhesive element.

3. The absorbent pad of claim 1, wherein the absorbent system comprises an absorbent core.

4. The absorbent pad of claim 3, wherein the absorbent system comprises an acquisition/distribution layer disposed over the absorbent core.

5. The absorbent pad of claim 3, wherein the absorbent core comprises at least one of cellulosic fibers and superabsorbent material.

6. The absorbent pad of claim 1, wherein the backsheet comprises at least one of a polymeric film layer and a nonwoven material layer.

7. The absorbent pad of claim 1, wherein the topsheet comprises a nonwoven material.

8. A method of forming an absorbent pad, comprising the steps of: forming a liquid pervious topsheet from a topsheet material web; forming a liquid impervious backsheet from a backsheet material web, forming a layered structure comprising an absorbent system disposed between the backsheet and the topsheet, the layered structure having a front edge, a back edge, a first side edge extending in a straight line from the front edge to the back edge and a second side edge extending in a straight line from the front edge to the back edge; attaching an elastic element to at least one of the topsheet and the backsheet along each of the first and second side edges of the layered structure so that the elastic element is disposed between the topsheet and the backsheet, the elastic elements generating a cupping action so that the absorbent pad is biased towards a cup-like shape; attaching a first side adhesive element to the layered structure inwardly from the first side edge of the layered structure and extending along the first side edge; attaching a second adhesive element to the layered structure inwardly from the second side edge of the layered structure and extending along the second side edge; and attaching a central adhesive element to the layered structure between the first and second side adhesive elements, the absorbent pad having a first configuration in which the central adhesive element is releasably attached to an inner surface of an undergarment so that the absorbent pad retains its cup-like shape and a second configuration in which the first and second side adhesive elements are releasably attached to an outer surface of the undergarment to overcome the cupping action of the elastic elements; wherein the first and second side edges extend in said straight lines when the cupping action is overcome or when the pad is in a flat configuration.

9. The method of claim 8, further comprising the steps of:
covering the first side adhesive element with a first side peel strip;
covering the second side adhesive element with a second side peel strip; and
covering the central adhesive element with a central peel strip.

10. The method of claim 8, wherein the step of forming the layered structure comprises laminating the topsheet, backsheet and absorbent system together to form a unitary structure.

11. The method of claim 8, wherein the absorbent system comprises an absorbent core.

12. The method of claim 11, wherein the absorbent system comprises an acquisition/distribution layer disposed over the absorbent core.

13. The method of claim 8, wherein the topsheet material comprises a nonwoven material layer.

14. The method of claim 8, wherein the backsheet material comprises at least one of a nonwoven material layer and a polymeric film layer.

* * * * *